United States Patent [19]

Hauschka et al.

[11] Patent Number: 5,616,576
[45] Date of Patent: Apr. 1, 1997

[54] CONTROLLING BONE RESORPTION WITH PYRROLOQUINOLINE QUINONE (PQQ) AND RELATED COMPOUNDS

[75] Inventors: Peter V. Hauschka, Needham; Paul M. Gallop, Chestnut Hill, both of Mass.

[73] Assignee: The Children's Medical Center Corporation, Boston, Mass.

[21] Appl. No.: 274,193

[22] Filed: Jul. 12, 1994

[51] Int. Cl.[6] .......................... A61K 31/675; A61K 31/44
[52] U.S. Cl. ............................. 514/81; 514/108; 514/292
[58] Field of Search .................................. 514/292, 108, 514/81

[56] References Cited

U.S. PATENT DOCUMENTS 4,898,870  2/1990  Narutomi ................................. 514/292
5,061,711 10/1991  Urakami ................................. 514/292

OTHER PUBLICATIONS

Beard et al., J. Lab. Clin. Med. 108:498–505 (1986).
Beug et al., Cell 18:375–390 (1979).
Cole and Walters, J. Histochem. Cytochem. 35:203–206 (1987).
Gallop et al., Connective Tissue Research 27:74 (1992).
Garrett et al., J. Clin. Invest. 85:632–639 (1990).
Key et al., Bone 11:115–119 (1990).
Krukowski and Kahn, Calci, Tissue Int. 34:474–479 (1982).
Takahashi et al., Endocrinology 122:1373–1382 (1988).
MacIntyre et al., Proc. Natl. Acad. Sci. USA 88:2936–2940 (1991).
Ries et al., J. Bone Miner. Res. 7:931–939 (1992).

*Primary Examiner*—Theodore J. Criares
*Attorney, Agent, or Firm*—Fish & Richardson P.C.

[57] ABSTRACT

PQQ and PQQ-generating compounds inhibit osteoclast cell formation and bone resorption, and those compounds can be used to treat medical conditions characterized by undesired bone resorption. PQQ-phosphonates that target osteoclasts at the bone-mineral interface are particularly useful in this regard.

14 Claims, 8 Drawing Sheets

CONTROLLING BONE RESORPTION WITH PYRROLOQUINOLINE QUINONE (PQQ) AND RELATED COMPOUNDS

STATEMENT AS TO FEDERALLY SPONSORED RESEARCH

This invention was funded at least in part by a grant from the United States government, and the government has certain rights in the invention.

1. Field of the Invention

This invention relates to controlling bone resorption.

2. Background of the Invention

Undesired bone resorption characterizes various clinical disorders discussed in greater detail below, including osteoporosis and certain periodontal and joint diseases.

Both physiological and pathological bone resorption involve osteoclasts, giant multinucleated cells that exhibit prodigious metabolic activity. Osteoclasts are derived by fusion of mononuclear cells of hemopoietic origin.

Osteoclast ontogeny and function is regulated by a variety of osteotropic hormones and cytokines. Reactive oxygen species are produced by osteoclasts during bone resorption, probably by way of metabolic reactions involved in the classical "respiratory burst" of neutrophils. Reactive oxygen species may also play a crucial role in bone resorption. It has been postulated that the respiratory activity of osteoclasts is related to bone resorptive activity. Fallone et al., *J. Bone Miner. Res.* 1(Suppl. 1):1 (1986). In addition, Beard et al., *J. Lab. Clin. Med.* 108:498–505 (1986) report that malignant infantile osteopetrosis, which is caused by a lack of normal osteoclastic function, is associated with defective superoxide production in neutrophils. Thereafter, Key et al., *Bone* 11:115–119 (1990) identified the superoxide anion between the external osteoclastic membrane and the bone, and Garrett et al., *J. Clin. Invest.* 85:632–639 (1990) and Ries et al., *J. Bone Miner. Res.* 7:931–939 (1992) have suggested that oxygen-derived free radicals, especially the superoxide anion, are associated with osteoclastic bone resorption.

Gallop et al. propose a mechanism for the formation and removal of the neutral radical, nitric oxide, which involves the putative redox-vitamin, PQQ [pyrroloquinoline quinone], and speculate about new therapeutic strategies for the control and prevention of maturity-onset, post-menopausal and senile osteoporosis as follows:[1]

". . . we proposed that the putative redox-vitamin, PQQ [pyrroloqinoline quinone], in concert with ascorbate, play a key role in the formation and removal of nitric oxide. Since such a process is likely to be subject to nutritional, hormonal, and pharmacological manipulation, we anticipate that this will lead to the development of new therapeutic strategies for the control and prevention of maturity-onset, post-menopausal and senile osteoporosis."

[1] Chemistry and Biology of Mineralized Tissues, PROCEEDINGS OF THE FOURTH INTERNATION CONFERENCE ON THE CHEMISTRY AND BIOLOGY OF MINERALIZED TISSUES; Coronado, Calif., Feb. 5–9, 1992, pp. 3529–38, Slavkin, H. and Price, P., Eds, Elsevier Science Publishers (1992).

MacIntyre et al. *Proc. Nat'l. Acad. Sci. USA*, 88:2936–2940 (1991) report that nitric oxide is liked to the inhibition of osteoclastic bone resorption.

Gallop et al. *Connective Tissue Research*, 27:74 (1992) say,

"We shall consider possible roles for PQQ in nitric oxide . . . biosynthesis from arginine and in NO removal by superoxide. Nitric oxide has now ben linked to the inhibition of osteoclastic bone resorption [citing MacIntyre et al.]."

Current strategies for controlling undesired bone resorption include dietary enhancement of minerals (particularly calcium). Other therapies include hormonal (e.g., estrogen-progestin) regimens to enhance bone formation or agents (such as salmon calcitonin or bisphosphonates) to block osteoclast formation.

SUMMARY OF THE INVENTION

We have demonstrated that PQQ and PQQ-containing compounds inhibit osteoclast cell formation and bone resorption. These compounds are therefore useful for treating undesired bone resorption. Without wishing to bind ourselves to a specific molecular mechanism, it appears that this inhibition is related to the compounds' ability to scavenge superoxide.

Accordingly, one aspect of the invention generally features treating undesired bone resorption by administering PQQ or a PQQ-containing compound. We use the term PQQ-containing compound to refer to PQQ itself, alternative redox forms of PQQ, derivatized PQQ, e.g., PQQ esters and phosphonates, and compounds that are metabolized to yield PQQ. Specific compounds that are used and the medical indications for their use are described in greater detail below.

We have also discovered that PQQ can be selectively targeted to osteoclasts at the bone mineral interface using compounds which link PQQ by a cleavable bridge to at least one phosphonate group. Accordingly, a second aspect of the invention generally features PQQ-phosphonate fusions, having the following general formula:

$$PQQ\text{-}L\text{-}CR_1R_2PO_3H$$

In that general formula, L is a cleavable bridge group comprising from 1–8 carbons. Preferably, L is subject to enzymatic cleavage from PQQ by an enzyme present in osteoclasts. When L is linked to a carboxyl group of PQQ, the enzyme is an esterase. $R_1$ is —H or an alkyl or aryl group or a substituted alkyl or aryl group, having from 1–8 (most preferably from 1–3) carbons. $R_2$ is either a second —$PO_3H$ group (making the compound a bis phosphonate PQQ derivative), or it is independently selected from —H or the $C_{1-8}$ groups that define $R_1$.

Other features and advantages of the invention will be apparent from the following Detailed Description.

DESCRIPTION OF THE PREFERRED EMBODIMENTS

A. Medical Indications

The invention applies to medical indications that are characterized by undesired bone resorption. It specifically applies to treating patients who present postmenopausal (Type I) osteoporosis, senile (Type II) osteoporosis, idiopathic juvenile osteoporosis, cytokine-mediated osteolytic disorders occurring in periodontal disease, joint disease (osteoarthritis, rheumatoid arthritis), bone metastasis, and Paget's disease of bone.

B. Compositions

1. The PQQ Component

The PQQ component according to the invention can be free PQQ (2,7,9-tricarboxy-pyrroloquinoline quinone, also termed methoxatin or 2,7,9-tricarboxy-1H-pyrrolo(2, 3f)quinoline-4,5-dione). The invention also includes administration of alternative redox forms of PQQ—e.g., the semiquinone or the fully reduced hydroquinone—as well as salts (e.g., $Na^+$ or $K^+$) of PQQ. The invention also includes administration of various PQQ derivatives that provide the PQQ redox function, either directly or after metabolism to yield PQQ, such as PQQ esters in which one or more of the PQQ carboxyl groups is esterified, preferably as a short aliphatic ester, such as an ester of six or less carbons, and, most preferably, the methyl, ethyl, or butyl ester. These compounds can generally be prepared by the methods described in Urakami U.S. No. 5,061,711 and Narutomi et al. U.S. No. 4,898,870; hereby incorporated by reference. Specifically mono- di- and tri-esters of PQQ involving one or more of the PQQ carboxyl groups are included. Lower ($C_1$–$C_4$) alkyl esters and alkenyl esters (including vinyl and allyl esters) are also included.

Other PQQ derivative such as the ones described below can be used. Candidate PQQ-related compounds may be screened for the requisite activity using one or more of the protocols described in detail in this application.

Particularly useful PQQ derivatives are the PQQ phosphonates. Specifically, the phosphonate function will target osteoclasts at the bone/mineral interface, thus enhancing local concentration and reducing the corresponding systemic concentration of the compound. Generally, the PQQ phosphonate adduct will be cleaved to yield PQQ locally, where it can act on the osteoclasts. The preferred method for cleavage is by a local enzyme, e.g., an esterase, produced by the osteoclast.

There are several ways to covalently attach PQQ to a phosphonate group. One attachment is via an ester linkage using one or more of PQQ's carboxyl functions. Such ester linkages can be prepared generally as described above regarding PQQ esters.

Figures 7A, 7B:
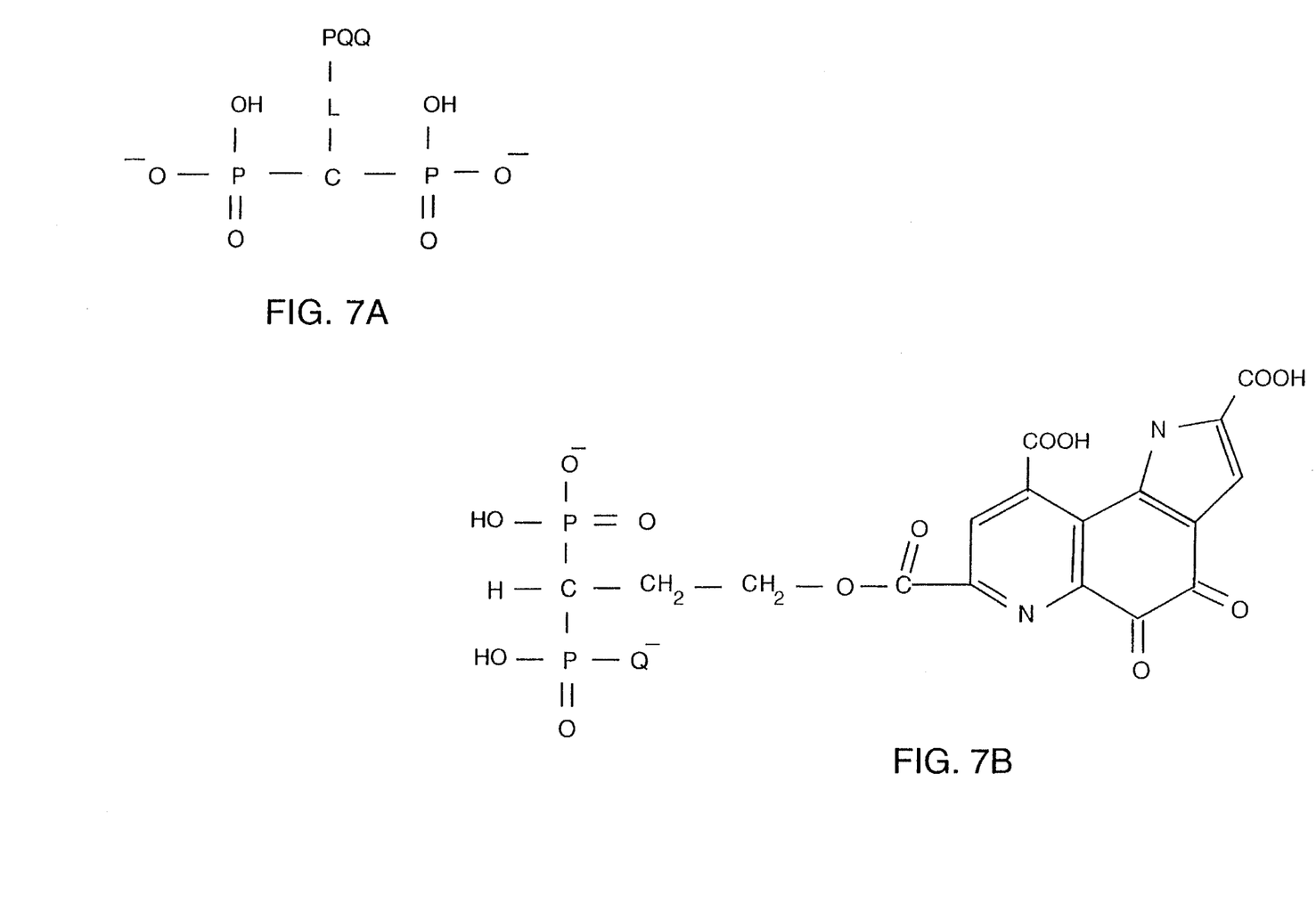
FIG. 7A is a generalized formula for PQQ phosphonates.
FIG. 7B is a formula for a specific PQQ bis phosphonate.

Esterases produced by the osteoclast generally will recognize and cleave these ester linkages. Thus, in the general formula of FIG. 7A, L is attached to one of the -COOH functions of PQQ. Where $L=(CH_2)_2$, as in FIG. 7B, the resulting molecule is a bis phosphonate substituted n-butyl ester of PQQ. Osteoclast esterases will specifically recognize this ester, cleaving it at the osteoclast site to yield PQQ. FIG. 7B illustrates a compound with one such monoester linkage. Clearly, the corresponding di- and tri-esters, or a mixture thereof, could be used.

C. Administration

The PQQ-related compound is formulated for delivery to the site where resorption is to be controlled. When the mode of administration is injection, the compound is formulated in a physiologically acceptable carrier such as buffered pyrogen-free saline.

The compound may be formulated in a slow release device, so as to deliver the compound for a prolonged period (e.g., over 12 hours and preferably over a week). The device is implanted at the site—e.g. for arthritis, at the joint or for dental applications at the tooth/soft tissue interface. Numerous suitable release systems are known.

D. Examples

The following examples illustrate the ability of the invention to control bone resorption. Specifically, we demonstrated the effect of PQQ, as a scavenger of superoxide, on osteoclast-like cell formation and on mature osteoclast function.

EXAMPLE 1. HD-11 Cells

HD-11 is a v-myc-transformed chicken myelomonocytic cell line[2] that can serve as an osteoclastic model system because of its expression of osteoclastic markers in response to 1,25-dihydroxy vitamin D3 (1,25-$(OH)_2$D3). The specific markers it develops are tartrate-resistant acid phosphatase (TRAP)[3] and 121F and 75B osteoclast-specific surface antigens. HD-11 cells for use in the experiments described below can be obtained from known sources. These cells were maintained in 75-$cm^2$ tissue culture flasks in Dulbecco's modification of Eagle's medium supplemented with 4 mM glutamine, 10% fetal calf serum, and penicillin/streptomycin (DMEM/FCS, Gibco, Grand Island, N.Y.) at 37° C. in a humidified atmosphere of 5% $CO_2$ and 95% air.

[2] Created by infecting chicken bone marrow cells with MC29 leukemia virus. See, Beug et al. Cell 18:375–390 (1979).

[3] TRAP, is a marker enzyme that is obligatory for osteoclasts. TRAP is one of the lysosomal acid hydrolases which is synthesized and released from osteoclasts.

EXAMPLE 2. Chicken osteoclasts and bone marrow cells

We isolated chicken osteoclasts and bone marrow cells by a modification of the methods described by Takahashi et al., *Endocrinology* 122:1373–1382 (1988). Chicken osteoclasts were isolated from the bone marrow of chick tibias between day 16 and day 19 of embryonic development. Fertile white leghorn chicken eggs (Spafas, Conn.) were incubated at 37° C., 65% relative humidity in an egg incubator. Embryonic chick tibias were sectioned longitudinally and the bone marrow was mechanically curetted into cold serum-free HEPES-buffered Medium 199. The resulting cells in suspension were collected by centrifugation and resuspended in HEPES-buffered Medium 199 with 10% fetal calf serum and antibiotics (M-199/FCS, Gibco, Grand Island, N.Y.).

EXAMPLE 3. Assay by NBT of reduction of superoxide in HD-11 cell culture

Figure 1:
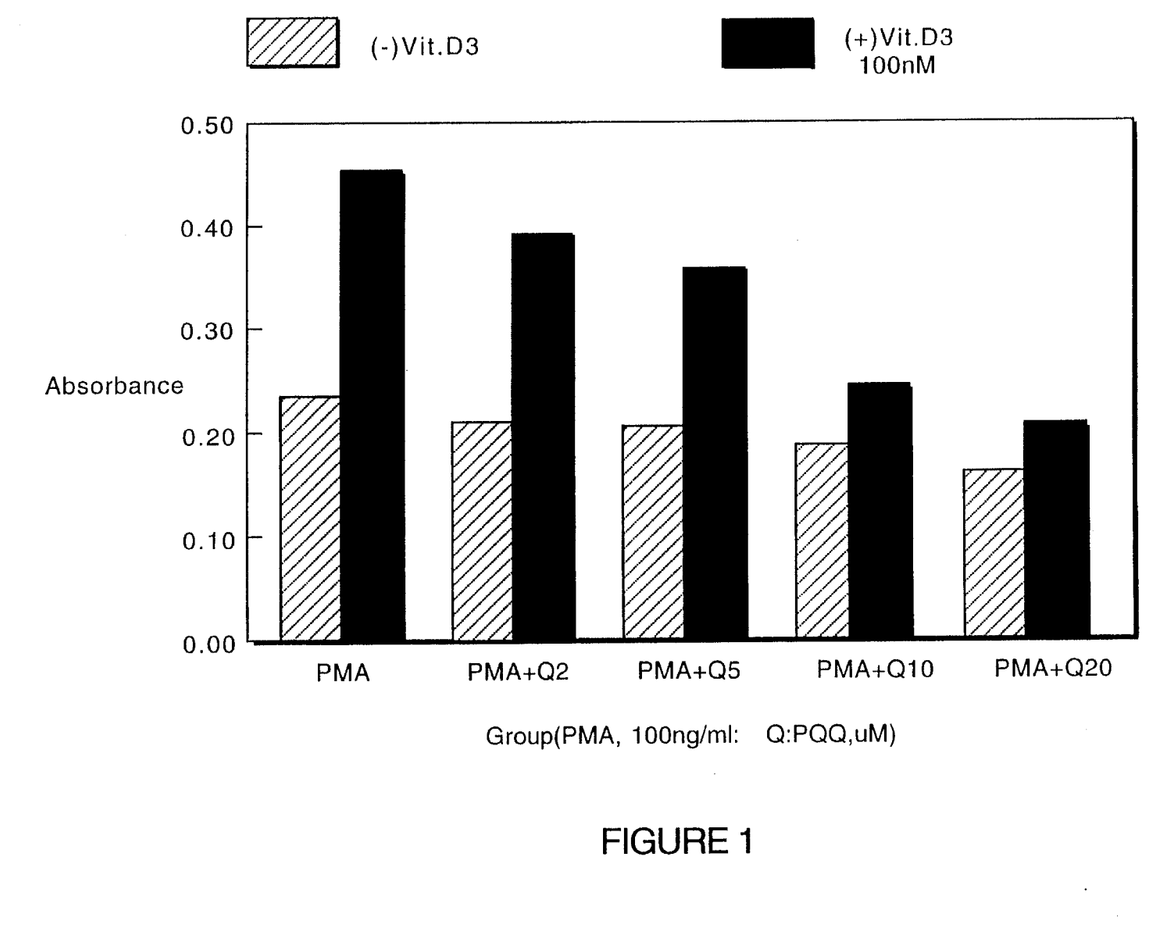
FIG. 1 is a bar graph depicting the effects of PQQ on phorbol myristate acetate (PMA)-induced nitroblue tetrazolium (NBT) reduction in HD-11 cells, as described in Example 3, below.

To determine whether PQQ scavenges superoxides, we stained HD-11 cells described above with nitroblue tetrazolium (NBT) as a superoxide detection method, with the results shown in FIG. 1. Specifically, HD-11 cells were plated at a density of 4–5×10⁴/cm² in 96-well tissue culture plates and cultured in DMEM/FCS. Fresh medium supplemented with 100 nM 1,25-(OH)$_2$D3 (Biomol, Plymouth Meeting, Pa.) (+VD3=cross-hatched bars line in FIG. 1) or vehicle (0.087%(v/v) final ethanol concentration) (−VD3= slanted lines in FIG. 1) was added when the cells reach confluency. After 24 h of culture, the cells were pretreated with PQQ (0–20 uM) in fresh DMEM/FCS for 45 min. The cells were then washed with warm PBS and incubated for 2 h in Hank's balanced salt solution (HBSS) containing 1 mg/ml nitroblue tetrazolium (NBT) in the presence of PQQ (0, 2 μM, 5 μM, 10 μM, and 20 μM) and 100 ng/ml phorbol myristate acetate (PMA). Stained cells were fixed with 2.5% formalin for 2 min and rinsed with PBS. Each well of the 96-well tissue culture plate was read at 595 nm by spectrophotometry (UVmax kinetic microplate reader, Molecular Devices, Menlo Park, Calif.).

FIG. 1 shows the effect of PQQ on PMA-induced NBT reduction in HD-11 cell culture. Specifically, HD-11 cells, activated by 100 ng/ml PMA, reduced yellow NBT dye to an insoluble purple formazan by means of superoxide generated during the respiratory burst. NBT reduction activity in HD-11 cells is increased by the addition of 100 nM 1,25-(OH)2D3, which is a known activator of NADPH oxidase. PQQ inhibited the 1,25-(OH)$_2$D3-induced NBT reduction in a dose-dependent manner. The maximal effect of PQQ (20 μM) on NBT reduction was found to be 42% inhibition in the nontreated group and 52% inhibition in the 1,25-(OH)2D3-treated group.

EXAMPLE 4. Quantitative histochemical TRAP assays of HD-11 cells

We examined the effect of PQQ on vitD3-induced TRAPP induction in HD-11 cells. The results are shown in FIG. 2.

Specifically, HD-11 cells were cultured in DMEM/FCS on 13 mm in diameter tissue culture coverslips (Lux, Nunc, Inc., Ill.) placed in 6-well tissue culture plates. When the cells reached 50–70% confluence, fresh medium containing 10 nM 1,25-(OH)$_2$D3 or vehicle in the presence or absence of PQQ (20 uM) was added. After 24 h of incubation, the HD-11 cells were washed with warm PBS, air-dried at 4° C., and fixed with 3.7% formalin fumes for 5 min. See Cole and Walters, *J. Histochem. Cytochem.* 35:203–206 (1987). For the determination of TRAP-positive cells, cultures were stained using a commercial kit (Sigma) according to the directions using naphthol AS-BI phosphate (0.125 mg/ml) as a substrate. After TRAP staining, the cells were counterstained with 0.02% aqueous Fast Green FCF for 2 min. TRAP-positive HD-11 cells were counted from five randomly selected fields and expressed as a percentage of the total cells counted in each field using light microscopy (Nikon, HFX).

Figure 2:
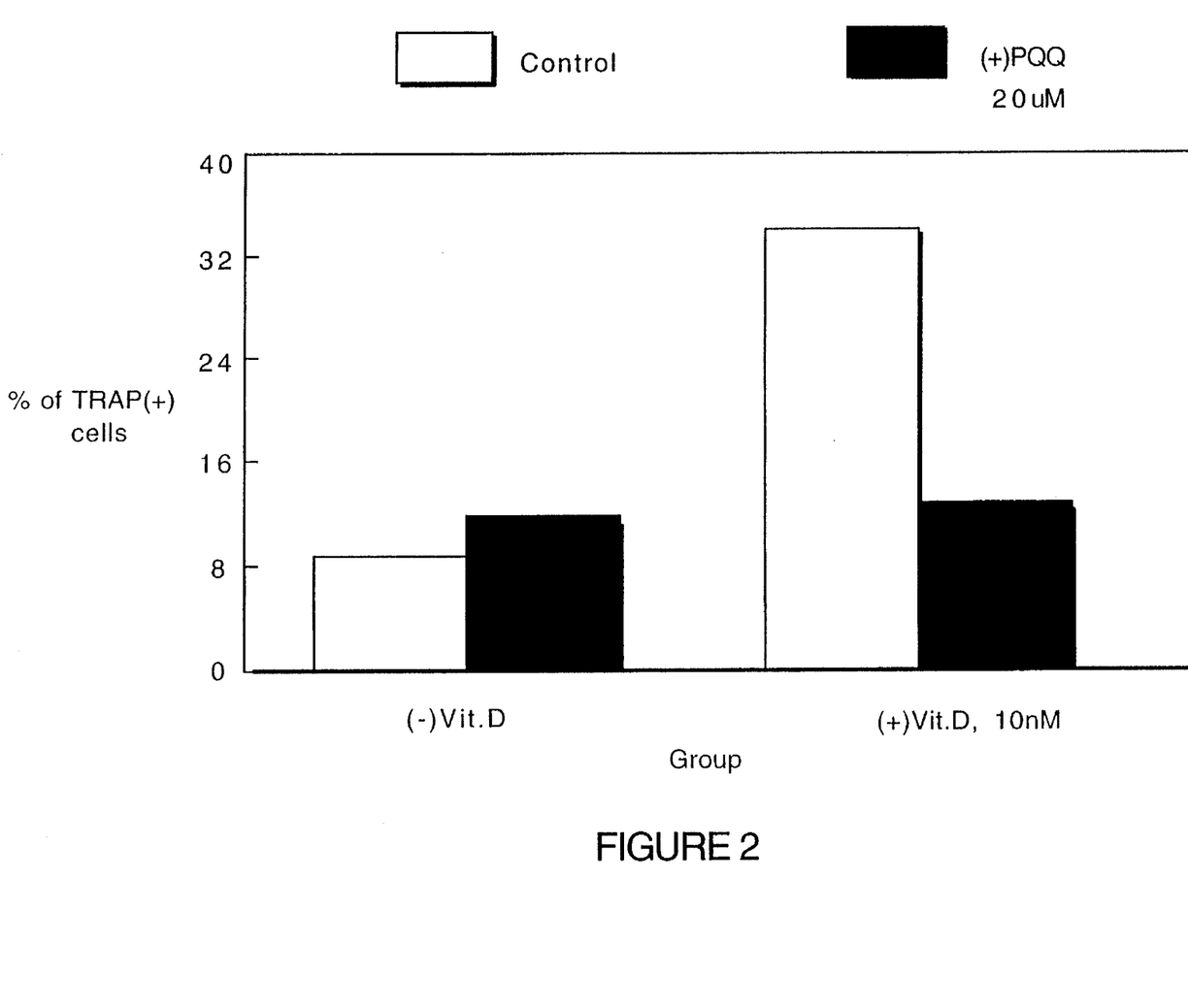
FIG. 2 is a bar graph depicting the effects of PQQ on vitamin D3-induced tartrate resistant acid phosphatase (TRAP)$^+$ cell formation in HD-11 cell culture, as described in Example 4, below.

As shown in FIG. 2, the addition of 20 μM PQQ inhibited TRAP⁺ expression in HD-11 cells.

EXAMPLE 5. Osteoclast-like cell formation from bone marrow cells

We examined the effect of PQQ on vitD3-induced TRAP-positive multinucleated cell formation of chick bone marrow cells. The results are shown in FIG. 3.

Specifically, bone marrow cells, isolated from chick embryonic tibial bone marrow as described above, were plated in 8-well chamber slides (Nunc Inc., Naperville, Ill.) and cultured in 0.4 ml of M-199/FCS for 24 h. After the nonadherent cells were removed by rinsing the well with M-199/FCS three times, the remaining cells were treated with 10 nM 1,25-(OH)$_2$D3 containing the appropriate PQQ concentration (0–20 uM) and cultured for 7 d. Medium was changed every other day by replacing 0.2 ml old medium with fresh medium containing the corresponding concentration of 1,25-(OH)$_2$D3 and PQQ. After 7 d of culture, the cells were stained for TRAP using the same method as for HD-11 cells. Total TRAP-positive multinucleated cells (containing three or more nuclei) which were formed from bone marrow cells were counted over the entire culture surface of the well. To verify that PQQ was affecting TRAP expression and had no direct inhibitory effect on the TRAP activity itself, control studies were performed by pretreating the culture with 20 uM PQQ for 1 h just before TRAP staining.

Figure 3:
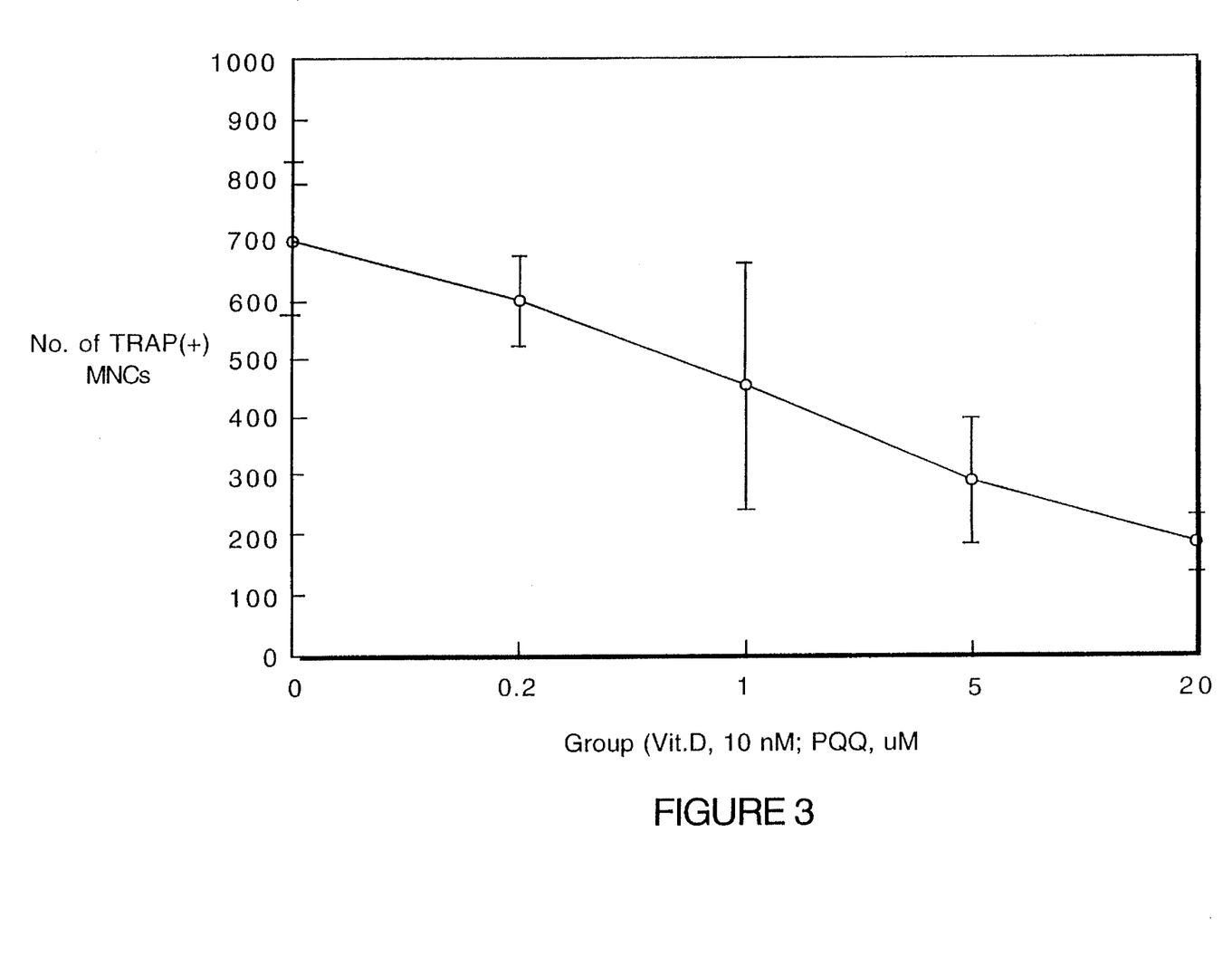
FIG. 3 is a graph of the effect of PQQ on TRAP$^+$ multinucleated cell formation in chicken bone marrow cell culture, as described in Example 5, below.

As shown in FIG. 3, PQQ inhibited formation of TRAP⁺ cells in a dose dependent manner.

EXAMPLE 6. Dentin resorption assay a. in vitro

Figure 4:
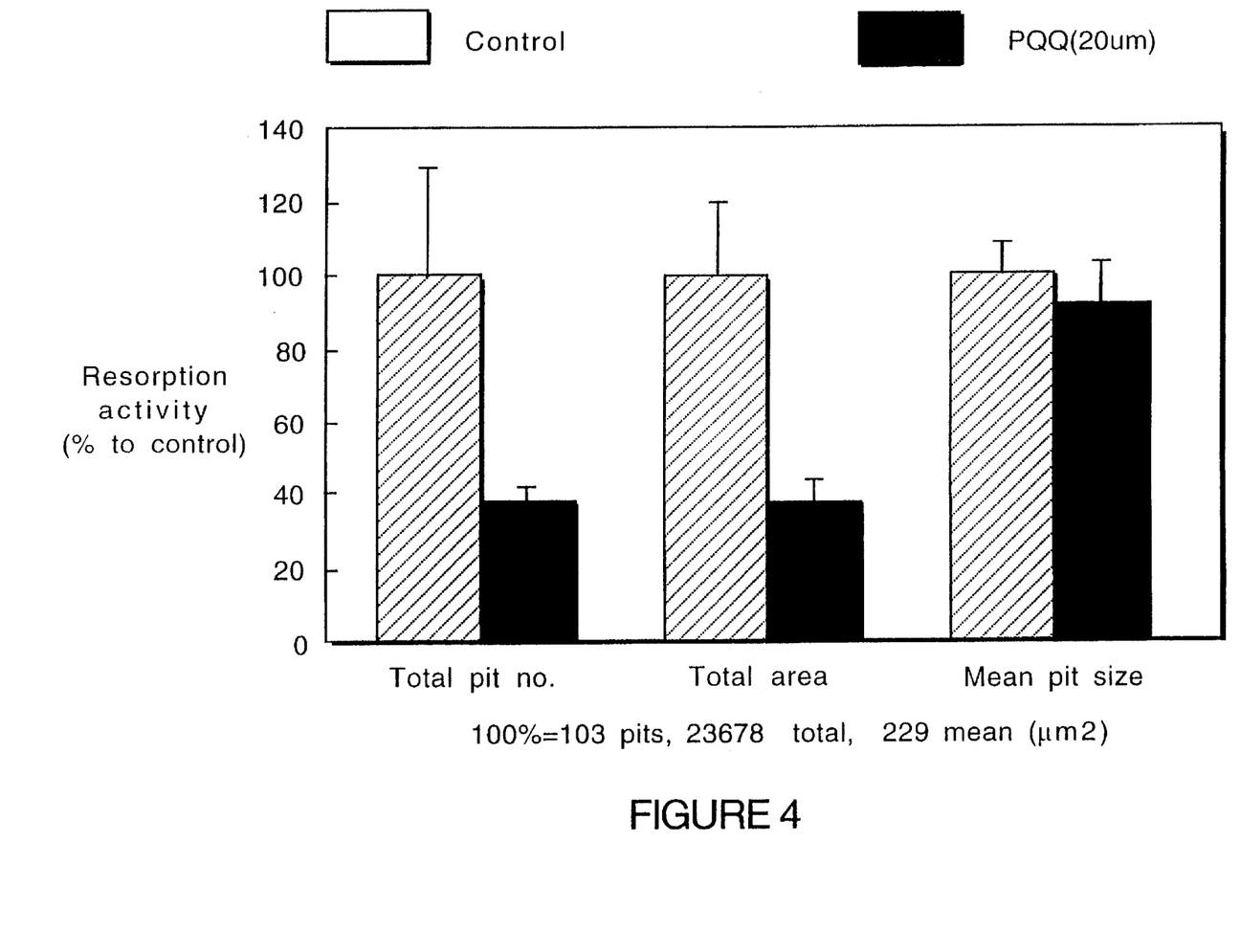
FIG. 4 is a bar graph of the effect of PQQ on dentin resorption in chicken osteoclast culture, as described in Example 6a, below.

As shown in FIG. 4, we studied the effect of PQQ on dentin resorption in vitro by mature chicken osteoclasts. Specifically, marrow cells obtained as described above were plated on sterile 4×4 mm polished pilot whale dentin slices and mature osteoclasts were allowed to attach for 30 min. The remaining unattached cells were collected and replated in 60 mm culture dishes for 6 h to capture all of the mature cells. Finally, the unattached, immature mononuclear precursor cells were collected and cultured in M-199/FCS for the assay of osteoclast-like cell formation Pilot whale (*Globicephala melaena*) teeth were kindly provided by Dr. G. Early (Director of the New England Aquarium Marine Mammal Stranding Program) with U.S. Government permission. Teeth were cut into uniform dentin slices (4×4 mm), and the dentin slices were washed with 70% ethanol and sterilized under u.v. light. Chick osteoclasts, isolated from embryonic tibiae, were seeded on the dentin slices, allowed to attach for 30 min, and cultured in the presence or absence (control) of 20 uM PQQ for 18 h. After culture, cells were removed from the dentin slices by treatment of 1M ammonium hydroxide for 30 min and sonication for 3 min. Dentin slices were rinsed with absolute ethanol, air dried, and gold sputter coated for inspection by scanning electron microscopy (SEM, JEOL, T-200). The dentin resorption area was traced from the SEM monitor and the area of each resorption pit was measured using a computer program (Image, version 1.40, produced by Wayne Rasband, NIH).

The presence of PQQ resulted in a significant decrease in dentin resorption in terms of the total resorption area (23,680±4,940 μm², control vs. 8150±1,370 μm², at 20 μM PQQ) and the number of resorption pits per 16 mm² dentin slice (103.5±29.3 vs. 38.3±5.2 at 20 μM PQQ). However, the mean area of each resorption pit was essentially unaffected by the addition of 20 μM PQQ. An interesting morphological characteristic of the resorption pits made in the presence of PQQ was the existence of a mat of exposed and undigested collagen fibrils suggestive of a PQQ-dependent inhibition of collagen proteolysis. Control pits were smooth and free of fibrillar material.

b. in ovo

Figure 5:
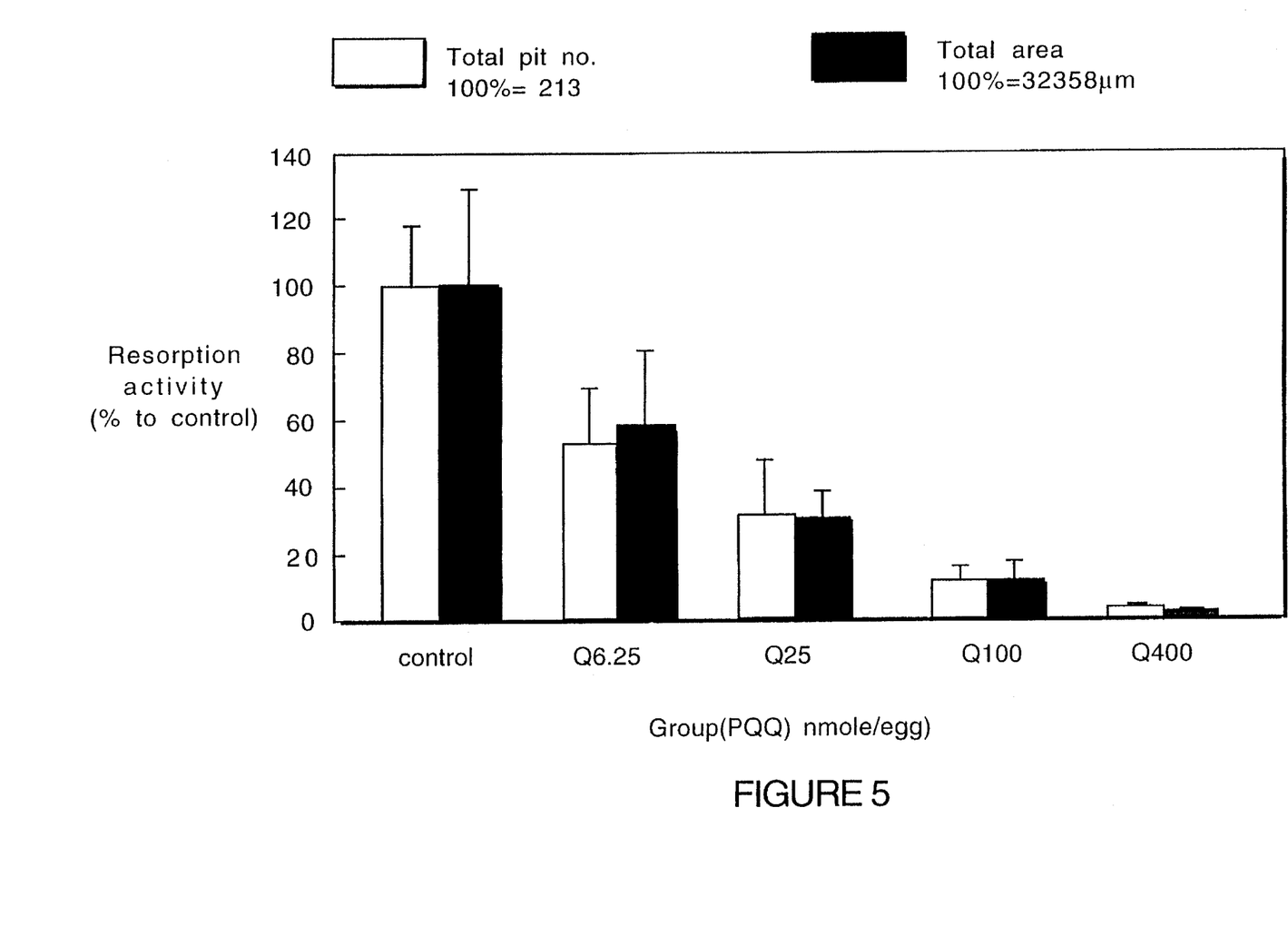
FIG. 5 is a bar graph of the effect of PQQ on dentin resorption by chicken osteoclasts in ovo, as described in Example 6b, below.
Figure 6A:
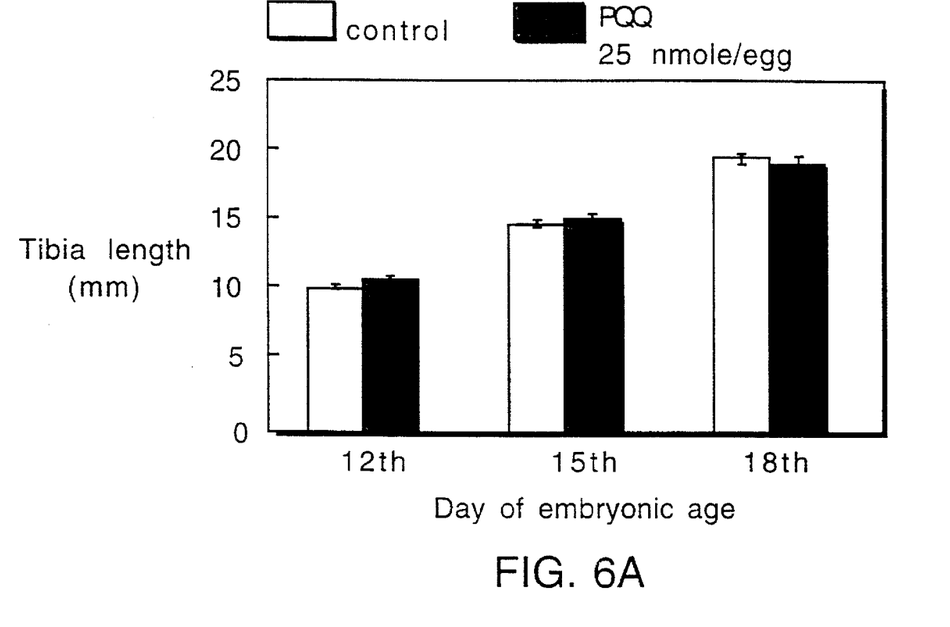
FIGS. 6A–6D are bar graphs of the effects of PQQ on tibial growth and chicken embryo growth, as described in Example 7, below.
Figure 6B:
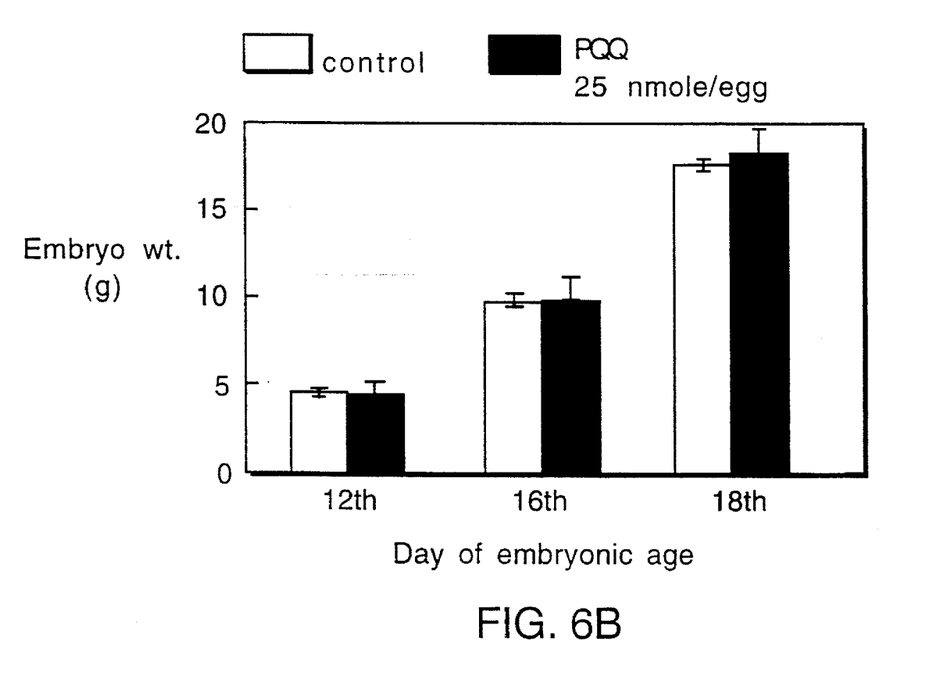
Figure 6C:
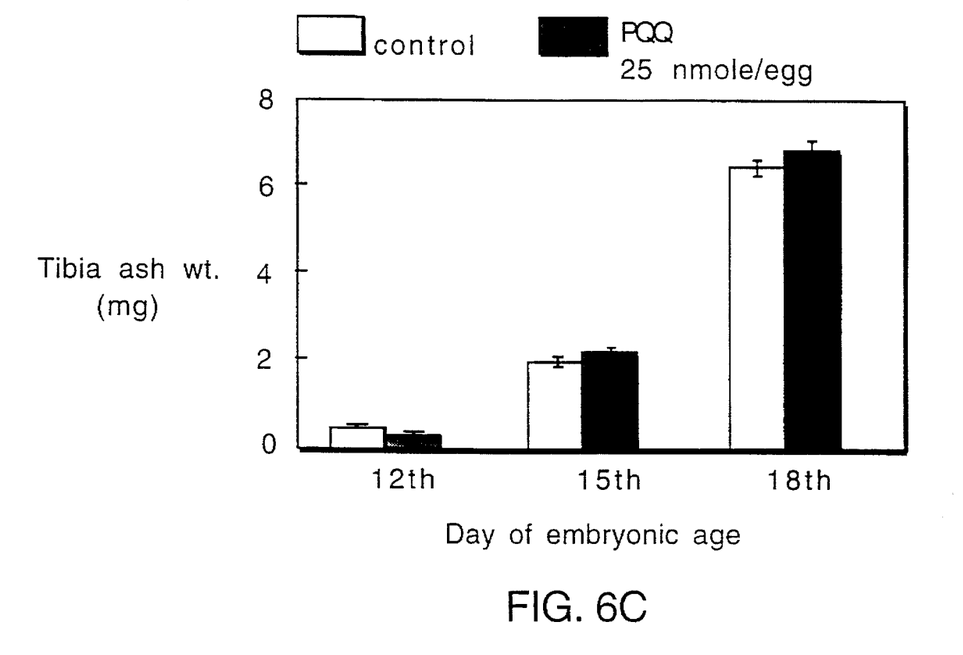
Figure 6D:
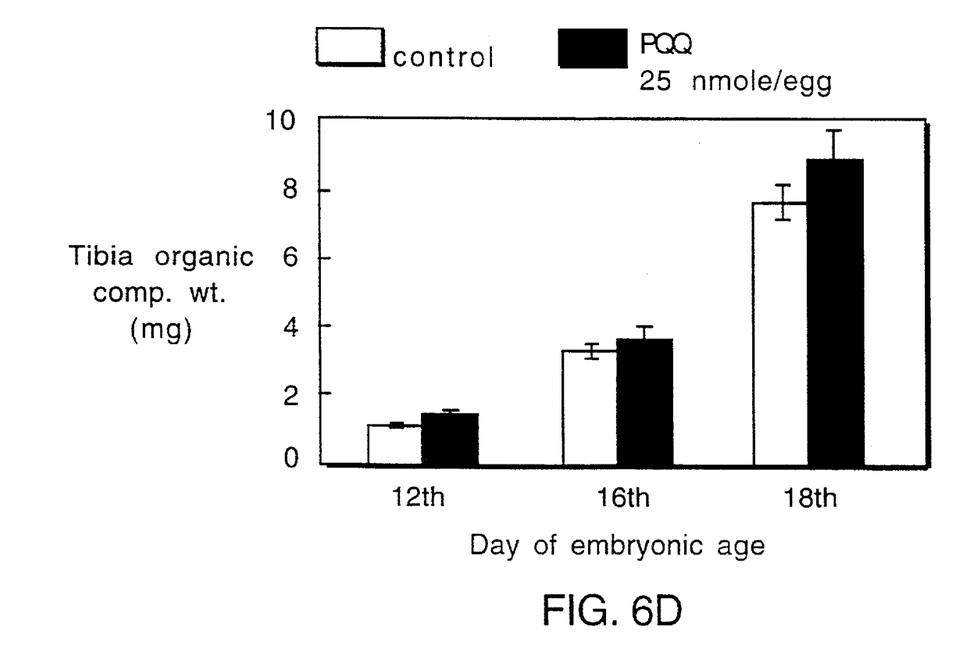

As shown in FIG. 5, we studied the effect of PQQ on dentin resorption in ovo, using chicken eggs. Dentin resorption assay was performed by the modified method of Krukowski and Kahn, *Calci. Tissue Int.* 34:474–479 (1982). In brief, chicken eggs were windowed with a sterile blade at the day 3 of fertilization and the windows were sealed with autoclaved tape. After 5 days of incubation, PQQ (0–400 nmole in 0.2 ml PBS) was administered to the eggs, and dentin slices (4×4 mm) were placed onto the surface of the chorioallantoic membrane (CAM) through the window. After 7 days of incubation, dentin slices were harvested and observed under the SEM. Treatment with PQQ decreased the dentin resorption in a dose-dependent fashion.

EXAMPLE 7. Measurement of embryonic chicken tibia

We determined the effect of PQQ on the development of embryonic chicken tibia in two ways: 1) by single administration of PQQ (0–100 nmole/egg), and 2) by multiple administration of PQQ (25 nmole/egg, every other day). Fertile chicken eggs were windowed as described above, and PQQ was administered through the window at the day 9 of fertilization only, or on day 9 and alternate days thereafter. After 9 days of incubation (or 3, 6, and 9 days for the multiple injection experiments, chicken embryos were weighed and the intact tibiae were surgically removed. Tibia length and wet weight were measured, and then the bones were dried at 110° C. for 25 h to measure the dry weight. After weighing the dried tibiae, the specimens were ashed in a 600° C. furnace for 24 h and reweighed. The weight of organic components was calculated by subtraction of the ash weight from the dry weight.

Tables 1 and 2, and FIGS. 6A–6D report the results of these experiments. In Table 1, 100 nmole/egg (c.a. 2 μM in a 50 g egg) showed a modest tendency to stimulate tibia weight (+5.5% dry weight, +7.8% organic weight), whereas lower concentrations of PQQ (6.25 and 25 nmole/egg) showed a slight inhibitory effect. FIGS. 6A–6D and Table 2 show that multiple administration of PQQ caused increases of 16% and 10% in bone weight at days 15 and 18 after fertilization, respectively. Of particular significance is the 15 day organic weight which increased in the presence of PQQ to 119% of the control. While not wishing to bind ourselves to a particular molecular mechanism, it appears that the increase in bone weight is probably linked to the inhibitory effects of PQQ on the differentiation and activation of osteoclasts.

| Group | Embryo (g) wt. | Tibia (mm, mg) | | | |
|---|---|---|---|---|---|
| | | length | dry wt. | Ash wt | Org. wt. |
| Control | 18.49 ± 1.22 | 19.29 ± 0.41 | 15.00 ± 0.65 | 7.30 ± 0.30 | 7.70 ± 0.36 |
| 6.25 | 14.02 ± 1.16 | 18.34 ± 0.40 | 13.60 ± 0.35 | 6.82 ± 0.16 | 6.78 ± 0.26 |
| 25 | 16.18 ± 1.02 | 19.53 ± 0.15 | 13.60 ± 0.56 | 6.64 ± 0.26 | 6.96 ± 0.32 |
| 100 | 18.24 ± 0.97 | 20.17 ± 0.74 | 15.83 ± 1.77 | 7.53 ± 0.78 | 8.30 ± 0.99 |

Group: PQQ nmole/egg.
Data are Mean ± S.E.M.

Effect of PQQ on the development of embryonic chicken tibia by single administration. PQQ was injected at the day of 9 and the tibiae were harvested at the day of 18.

| Days | Group | Embryo (g) wt. | Tibia (mm, mg) | | | |
|---|---|---|---|---|---|---|
| | | | length | dry wt. | Ash wt. | Org. wt. |
| 12 | c | 4.71 + 0.10 | 9.95 + 0.21 | 1.62 + 0.13 | 0.40 + 0.05 | 1.22 + 0.08 |
| | PQQ | 4.60 + 0.35 | 10.80 + 0.32 | 1.58 + 0.16 | 0.28 + 0.04 | 1.30 + 0.14 |
| 15 | c | 9.77 + 0.66 | 14.91 + 0.24 | 4.90 + 0.25 | 1.86 + 0.10 | 3.04 + 0.17 |
| | PQQ | 9.87 + 0.39 | 15.34 + 0.30 | 5.66 + 0.26 | 2.04 + 0.17 | 3.62 + 0.15 |
| 18 | c | 17.25 + 0.41 | 19.76 + 0.37 | 14.38 + 0.80 | 6.55 + 0.26 | 7.83 + 0.55 |
| | PQQ | 18.24 + 1.43 | 19.17 + 0.53 | 15.83 + 0.98 | 7.03 + 0.32 | 8.80 + 0.78 |

Data are Mean + S.E.M.

Effect of PQQ on the development of embryonic chicken tibia by multiple administration (every other day). PQQ was injected at the day of 9, 11, 13, 15, 17 and the tibjae were harvested at the day of 18.

What is claimed is:

1. A method of reducing undesired bone resorption in a patient by administering to said patient a bone-resorption decreasing amount of PQQ or of a compound that contains a PQQ group.

2. The method of claim 1 in which the patient is characterized by osteoporosis.

3. The method of claim 2 in which the patient is characterized by postmenopausal (Type I) osteoporosis.

4. The method of claim 2 in which the patient is characterized by senile (Type II) osteoporosis.

5. The method of claim 2 in which the patient is characterized by idiopathic juvenile osteoporosis.

6. The method of claim 1 in which the patient is characterized by a cytokine-mediated osteolytic disorder.

7. The method of claim 1 in which the patient is characterized by periodontal disease.

8. The method of claim 1 in which the patient is characterized by joint disease.

9. The method of claim 1 in which the patient is characterized by osteoarthritis.

10. The method of claim 1 in which the patient is characterized by rheumatoid arthritis.

11. The method of claim 1 in which the patient is characterized by bone metastasis of tumors.

12. The method of claim 1 in which the patient is characterized by Paget's disease of bone.

13. The method of claim 1 in which the compound administered is PQQ or a redox form thereof.

14. The method of claim 1 in which the compound administered is a PQQ ester.

* * * * *